United States Patent [19]

Doya et al.

[11] Patent Number: 5,349,077
[45] Date of Patent: Sep. 20, 1994

[54] PROCESS FOR PRODUCING ALKYLENE CARBONATES

[75] Inventors: Masaharu Doya; Takashi Ohkawa; Yutaka Kanbara; Aksushi Okamoto; Kenichi Kimizuka, all of Niigata, Japan

[73] Assignee: Mitsubishi Gas Chemical Company, Inc., Tokyo, Japan

[21] Appl. No.: 99,461

[22] Filed: Jul. 30, 1993

[30] Foreign Application Priority Data

| Jul. 31, 1992 | [JP] | Japan | 4-205362 |
| Jul. 31, 1992 | [JP] | Japan | 4-205363 |
| Jul. 31, 1992 | [JP] | Japan | 4-205364 |
| Jun. 30, 1993 | [JP] | Japan | 5-161857 |

[51] Int. Cl.$^5$ ............................................. C07C 69/96
[52] U.S. Cl. ..................................... 558/260; 549/229; 549/230
[58] Field of Search ................... 558/260; 549/229, 230

[56] References Cited

U.S. PATENT DOCUMENTS 2,773,881  12/1956  Dunn et al. ................. 260/340.2
5,003,084   3/1991  Su et al. ....................... 549/230

FOREIGN PATENT DOCUMENTS 0443758  8/1991  European Pat. Off. .

OTHER PUBLICATIONS

Chemical Abstracts, vol. 82, No. 23, Jun. 9, 1975, Columbus, Ohio; Sergio Fumasoni et al.

Primary Examiner—José G. Dees
Assistant Examiner—Joseph M. Conrad, III
Attorney, Agent, or Firm—Wenderoth, Lind & Ponack

[57] ABSTRACT

A process for producing alkylene carbonates which comprises reacting urea and glycols described by the general formula RCH(OH) CH$_2$ OH; wherein R represents hydrogen or an alkyl group containing 1 to 4 carbons, using a catalyst containing zinc, magnesium, lead or calcium at reduced pressures. The alkylene carbonates are produced with high yield easily using raw materials which are comparatively inexpensive with a mild reaction that does not involve explosive or hazardous materials.

6 Claims, No Drawings

PROCESS FOR PRODUCING ALKYLENE CARBONATES

BACKGROUND OF THE INVENTION

1. Field of the invention

The present invention relates to the production of alkylene carbonates. Alkylene carbonates are important materials as organic solvents, fabricating agents for synthetic fiber, raw materials for medicines or intermediates for dialkyl-carbonates.

2. Description of the Prior Art

Ethylene carbonate, one of the alkylene carbonates, is produced continuously by reacting ethylene oxide with carbon dioxide at about 240° C. and 140 atmospheres using a pyridine catalyst as described in U.S. Pat. No. 2773881. However, because this industrial process of reacting ethylene oxide with carbon dioxide involves the reaction of explosive ethylene oxide at high pressure, there is a danger of explosion, and various counter-measures against explosion are required in this process.

Hitherto, various other processes for producing alkylene carbonates have been proposed. The process of reacting an alkylene glycol and urea to produce alkylene carbonate is remarkable, because both raw materials are relatively inexpensive and 'alkylene carbonates' are easily produced therefrom. EP-A0443758 describes a process of reacting an alkylene glycol and urea at atmospheric pressure or higher either without catalyst or using a tin-containing catalyst. EP-A-0443758 shows an 84–99% selectivity of alkylene carbonate to reacted glycol, less than 66% conversion of glycol compared to theoretical conversion and less than 63% selectivity of alkylene carbonate to reacted urea. So a large part of the urea decomposes in this process.

SUMMARY OF THE INVENTION

The purpose of this invention is to provide a process for the high yield industrial production of alkylene carbonates from urea and glycol.

The inventor has been engaged in intensive research to attain the above stated purpose. It has been found that alkylene carbonate is produced in remarkably high yield by reacting urea and glycol at reduced pressures, and that excellent performance of this reaction is observed when catalysts containing zinc, magnesium, lead or calcium are used.

Thus, the present invention provides a process for producing alkylene carbonates from urea and glycols described by the general formula $RCH(OH)CH_2OH$; wherein R represents an alkyl group containing 1 to 4 carbons, at reduced pressures, and a process for producing alkylene carbonate from urea and glycols shown by the general formula $RCH(OH)CH_2OH$; wherein R represents hydrogen or an alkyl group containing 1 to 4 carbons, using a catalyst containing at least one metal selected from zinc, magnesium, lead and calcium.

The present invention provides exceedingly high yield of alkylene carbonates from urea and glycol. This process is an extremely good process because the alkylene carbonate is produced quite easily using raw materials which are comparatively inexpensive.

This process is also an industrially superior process because the alkylene carbonate is produced by a mild reaction that does not involve explosive or hazardous materials and because the produced alkylene carbonate and unreacted alkylene glycol remaining are easily separated so that the unreacted alkylene glycol may be re-used.

DETAILED DESCRIPTION OF THE INVENTION

The reaction of present invention is carried out by introducing a catalyst to a mixed solution of urea and glycol and by heating them at reduced pressures.

The glycol used as the raw material in this invention has the general formula of $RCH(OH)CH_2OH$; wherein R represents hydrogen or an alkyl group containing 1 to 4 carbons. Examples of suitable glycols include ethylene glycol, 1,2-propylene glycol and 1,2-butylene glycol.

The molar ratio of the glycol to urea is preferably in the range of 1 to 5. When the molar ratio is less than 1.0, the selectivity of urea to alkylene carbonate decreases due to the side reaction of urea with itself.

The catalyst used in this invention is not limited so long as it contains zinc and/or magnesium. Examples of suitable catalysts are the metal powder, oxide, hydroxide, inorganic salt, carbonate, hydrocarbonate and organic acid salts of zinc or magnesium. An organic compound of zinc, magnesium lead or calcium which exist in the reaction system, the product of the reaction of urea, glycol or alkylene carbonate with a zinc, magnesium, lead or calcium compound for example, can be used as the catalyst.

These metal powders or compounds can be used as the catalyst by themselves or by mixing two or more of the metal powders or compounds. The mixture of these metal powders or compounds with inert compounds or carriers, or carriers supporting these metal powders or compounds can also be used as the catalyst.

The amount of the catalyst used is not limited, however, the molar ratio of zinc or magnesium to urea is generally within the range of 0.0001 to 10, and the preferable range is from 0.001 to 1.0.

A solvent is not necessary to carry out the process of the present invention because usually the reaction is carried out under glycol rich conditions in order to obtain high selectivity of alkylene carbonate. However, a solvent that is inert under the reaction conditions may be used.

The reaction of the present invention is carried out by maintaining the mixture of urea, glycol and the catalyst at the reaction temperature and reduced pressure, simultaneously removing ammonia which is produced from the mixture as a byproduct of the reaction.

The ammonia may be removed by introducing inert gas to the reacted solution under the reaction conditions, the refluxing of glycol is more effective than introduction of inert gas at reduced pressures. The amount of the glycol refluxed is 1.0 to 100 mole per mole of ammonia produced.

The preferred temperature of the reaction of the present invention is from 120° to 200 °C. The reaction rate is small at temperature lower than 120° C., and the amount of byproduct is increased at temperature higher than 200 °C.

The reaction pressure depends on the reaction temperature and the composition of the reaction solution. The reaction can be carried out at atmospheric pressure or higher, however, the reaction is preferably carried out at reduced pressures of 40 to 600 mmHg absolute. Higher selectivity is obtained at reduced pressures especially when ethylene glycol is used as a raw material.

The reaction pressure is selected so that the glycol may be refluxed at the reaction temperature to remove the ammonia produced.

The reaction time depends on the kind of raw glycols, the molar ratio of glycol to urea, the type and amount of catalyst, the reaction temperature and amount of glycol refluxed etc.. Generally the reaction time is from 0.5 to 20 hours.

The alkylene carbonate produced is separated from the reaction solution after the reaction is completed by usual methods such as, for example, distillation.

EXAMPLES

The present invention will be explained in more detail by the following examples, which by no means limit the scope of the invention.

EXAMPLE 1

A 300-ml three-necked flask, equipped with a stirrer, reflux condenser and thermometer, was charged with 60.1 g (1.00 mole) of urea, 155.2 g (2.50 mole) of ethylene glycol and 1.5 g of magnesium oxide. The reaction was carried out at 145° C. for 4 hours at a pressure of 120 mmHg with stirring and refluxing to remove the ammonia produced. After the completion of the reaction, 184.8 g of reacted solution was obtained by cooling the reaction solution. Gas-chromatography analysis showed that the amount of unreacted ethylene glycol was 95.4 g and the amount of produced ethylene carbonate was 71.9 g.

The conversion of ethylene glycol was 38.5% (theoretical conversion is 40.0%). The selectivity of ethylene carbonate to the ethylene glycol reacted was 84.9%. The selectivity of ethylene carbonate to urea was 81.7% (the conversion of urea was 100%).

EXAMPLE 2

The same reactor as in Example 1 was charged with 60.1 g (1.00 mole) of urea, 155.2 g (2.50 mole) of ethylene glycol and 1.5 g of magnesium oxide. The reaction was carried out at 170° C. for 2 hours at a pressure of 290 mmHg with stirring and refluxing to remove the ammonia produced. After the completion of the reaction, 184.2 g of reacted solution was obtained by cooling the reaction solution. Gas-chromatography analysis showed that the amount of unreacted ethylene glycol was 96.5 g and the amount of produced ethylene carbonate was 70.0 g.

The conversion of ethylene glycol was 37.8% (theoretical conversion is 40.0%). The selectivity of ethylene carbonate to the ethylene glycol reacted was 84.1%. The selectivity of ethylene carbonate to urea was 79.5% (the conversion of urea was 100%).

EXAMPLE 3

The same reactor as in Example 1 was charged with 60.1 g (1.00 mole) of urea, 248.3 g (4.0 mole) of ethylene glycol and 7.5 g of magnesium oxide. The reaction was carried out at 145° C. for 3 hours at a pressure of 120 mmHg with stirring and refluxing to remove the ammonia produced. After the completion of the reaction, 216.5 g of reacted solution was obtained by cooling the reaction solution. Gas-chromatography analysis showed that the amount of unreacted ethylene glycol was 88.0 g and the amount of produced ethylene carbonate was 74.1 g.

The conversion of ethylene glycol was 24.3% (theoretical conversion is 25.0%). The selectivity of ethylene carbonate to the ethylene glycol reacted was 86.5%. The selectivity of ethylene carbonate to urea was 84.2% (the conversion of urea was 100%).

EXAMPLE 4

The procedure of Example 1 was followed except that 77.6 g (1.25 mole) of ethylene glycol was charged into the reactor. The reaction vessel was cooled after the reaction was stopped and 104.8 g of reaction solution was obtained. Gas-chromatography analysis showed that the amount of unreacted ethylene glycol was 19.0 g and the amount of produced ethylene carbonate was 81.5 g.

The conversion of ethylene glycol was 75.5% (theoretical conversion is 80.0%). The selectivity of ethylene carbonate to the ethylene glycol reacted was 98.0%. The selectivity of ethylene carbonate to urea was 92.6% (the conversion of urea was 100%).

COMPARATIVE EXAMPLE 1

A 300-ml three-necked flask, equipped with a stirrer, reflux condenser and thermometer, was charged with 60.1 g (1.00 mole) of urea, 155.2g (2.50 mole) of ethylene glycol and 1.5 g of dibutyl tin dilaurate. The reaction was carried out at 145° C. with stirring and charging with nitrogen gas for 4 hours at atmospheric pressure according to the method of EP-A-0443758. After the completion of the reaction, 177.9 g of reacted solution was obtained by cooling the reaction solution. Gas-chromatography analysis showed that the amount of unreacted ethylene glycol was 110.8 g and the amount of produced ethylene carbonate was 2.7 g.

The conversion of ethylene glycol was 28.6% (theoretical conversion is 40.0%). The selectivity of ethylene carbonate to the ethylene glycol reacted was 4.3%. The selectivity of ethylene carbonate to urea was 3.7% (the conversion of urea was 100%).

COMPARATIVE EXAMPLE 2

The procedure of Comparative Example 1 was followed except that 1.5 g of zinc oxide was charged into the reactor. The reaction vessel was cooled after the reaction was stopped and 176.3 g of reaction solution was obtained. Gas-chromatography analysis showed that the amount of unreacted ethylene glycol was 107.9 g and the amount of produced ethylene carbonate was 6.3 g.

The conversion of ethylene glycol was 30.5% (theoretical conversion is 40.0%). The selectivity of ethylene carbonate to the ethylene glycol reacted was 9.4%. The selectivity of ethylene carbonate to urea was 7.2% (the conversion of urea was 100%).

EXAMPLES 5-11

The procedure of Example 1 was followed except that different catalysts of zinc or magnesium were charged to the reaction vessel. The catalysts used and the results are shown in Table 1. The conversion of urea was 100% for each example of Table 1.

TABLE 1

| Example No. | Catalyst | Reacted solution | | | Glycol conversion | Carbonate selectivity | |
|---|---|---|---|---|---|---|---|
| | | Whole | Glycol | Carbonate | | to glycol | to urea |
| 5 | zinc powder | 182.9 g | 103.2 g | 60.2 g | 33.5% | 81.7% | 68.4% |
| 6 | zinc carbonate | 184.7 | 95.1 | 72.3 | 38.7 | 84.8 | 82.1 |
| 7 | zinc chloride | 183.9 | 95.3 | 71.5 | 38.6 | 84.1 | 81.2 |
| 8 | zinc acetate | 184.0 | 95.6 | 71.2 | 38.4 | 84.2 | 80.8 |
| 9 | zinc nitrate | 183.5 | 96.6 | 70.9 | 38.4 | 83.9 | 80.5 |
| 10 | magnesium oxide | 184.2 | 95.0 | 71.3 | 38.8 | 83.6 | 81.0 |
| 11 | magnesium acetate | 184.1 | 94.8 | 71.7 | 38.9 | 83.8 | 81.4 |

EXAMPLE 12

A 500-ml three-necked flask, equipped with a stirrer, reflux condenser and thermometer, was charged with 60.1 g (1.00 mole) of urea, 190.3 g (2.50 mole) of 1,2-propylene glycol and 1.5 g of zinc oxide. The reaction was carried out at 145° C. for 2 hours at the pressure of 165 mmHg with stirring and refluxing of the ammonia produced. The reaction vessel was cooled after the reaction was stopped and 218.4 g of reaction solution was obtained. Gas-chromatography analysis showed that the amount of unreacted 1,2-propylene glycol was 116.1 g and the amount of produced 1,2-propylene carbonate was 99.2 g.

The conversion of 1,2-propylene glycol was 39.0% (theoretical conversion is 40.0%). The selectivity of 1,2-propylene carbonate to the 1,2-propylene glycol reacted was 99.8%. The selectivity of 1,2-propylene carbonate to urea was 97.2% (the conversion of urea was 100%).

EXAMPLE 13

The same reactor as in Example 12 was charged with 60.1 g (1.00 mole) of urea, 304.4 g (4.00 mole) of 1,2-propylene glycol and 1.5 g of magnesium oxide. The reaction was carried out at 165° C. for 1 hour at the pressure of 350 mmHg with stirring and refluxing the ammonia produced. The reaction vessel was cooled after the reaction was stopped and 332.8 g of reaction solution was obtained. Gas-chromatography analysis showed that the amount of unreacted 1,2-propylene glycol was 229.8 g and the amount of produced 1,2-propylene carbonate produced was 98.5 g.

The conversion of 1,2-propylene glycol was 24.5% (theoretical conversion is 25.0%). The selectivity of 1,2-propylene carbonate to the 1,2-propylene glycol reacted was 98.5%. The selectivity of 1,2-propylene carbonate to urea was 96.5% (the conversion of urea was 100%).

EXAMPLE 14

The same reactor as in Example 12 was charged with 60.1 g (1.00 mole) of urea, 225.3 g (2.50 mole) of 1,2-butylene glycol and 7.5 g of zinc oxide. The reaction was carried out at 145° C. for 2 hours at the pressure of 120 mmHg with stirring and refluxing the ammonia produced. The reaction vessel was cooled after the reaction was stopped and 259.0 g of reaction solution was obtained. Gas-chromatography analysis showed that the amount of unreacted 1,2-butylene glycol was 137.2 g and the amount of produced 1,2-butylene carbonate produced was 113.2 g.

The conversion of 1,2-butylene glycol was 39.1% (theoretical conversion 40.0%). The selectivity of 1,2-butylene carbonate to the 1,2-butylene glycol reacted was 99.8%. The selectivity of 1,2-butylene carbonate to urea was 97.5% (the conversion of urea was 100%).

COMPARATIVE EXAMPLE 3

A 300-ml three-necked flask, equipped with a stirrer, reflux condenser and thermometer, was charged with 60.1 g (1.00 mole) of urea, 190.3 g (2.50 mole) of 1,2-propylene glycol and 1.5 g of dibutyl tin dilaurate. The reaction was carried out at 145° C. for 2 hours at atmospheric pressure with stirring and charging of nitrogen gas according to the method of EP-A-0443758. After the reaction, 232.7g of reacted solution was obtained by cooling the reactor. Gas-chromatography analysis showed that the amount of unreacted 1,2-propylene glycol was 146.48 and the amount of 1,2-propylene carbonate produced was 34.9g.

The conversion of 1,2-propylene glycol was 23.1% (theoretical conversion is 40.0%). The selectivity of 1,2-propylene carbonate to the 1,2-propylene glycol reacted was 59.3%. The selectivity of 1,2-propylene carbonate to urea was 34.2% (the conversion of urea was 100%).

COMPARATIVE EXAMPLE 4

The procedure of Comparative Example 3 was followed except that 1.5g of zinc oxide was charged to the reactor. The reaction vessel was cooled after the reaction was stopped and 227.2g of reaction solution was obtained. Gas-chromatography analysis showed that the amount of unreacted 1,2-propylene glycol was 146.4 g and the amount of produced 1,2-propylene carbonate was 34.9 g.

The conversion of 1,2-propylene glycol was 33.2% (theoretical conversion is 40.0%). The selectivity of 1,2-propylene carbonate to the 1,2-propylene glycol reacted was 66.7%. The selectivity of 1,2-propylene carbonate to urea was 56.2% (the conversion of urea was 100%).

EXAMPLE 15

A 300-ml three-necked flask, equipped with a stirrer, reflux condenser and thermometer, was charged with 60.1 g (1.00 mole) of urea, 114.2 g (1.50 mole) of 1,2-propylene glycol and 1.5 g of zinc oxide. The reaction was carried out at 175° C. for 3 hours at atmospheric pressure with stirring and refluxing of the produced ammonia. After the reaction, 141.4 g of reacted solution was obtained by cooling the reactor. Gas-chromatography analysis showed that the amount of unreacted 1,2-propylene glycol was 42.7 g and the amount of produced 1,2propylene carbonate was 91.0 g.

The conversion of 1,2-propylene glycol was 62.6% (theoretical conversion is 66.7%). The selectivity of 1,2-propylene carbonate to the 1,2-propylene glycol reacted was 94.9%. The selectivity of 1,2-propylene carbonate to urea was 89.1% (the conversion of urea was 100%).

COMPARATIVE EXAMPLE 5

The procedure of Example 15 was followed except that 1.5 g of dibutyl tin dilaurate was charged to the reactor according to the method of EP-A-0443758. The reaction vessel was cooled after the reaction was stopped and 42.9 g of reaction solution was obtained. Gas-chromatography analysis showed that the amount of unreacted 1,2-propylene glycol was 55.5 g and the amount of produced 1,2-propylene carbonate was 66.0 g.

The conversion of 1,2-propylene glycol was 51.4% (theoretical conversion is 66.7%). The selectivity of 1,2-propylene carbonate to the 1,2-propylene glycol reacted was 83.8%. The selectivity of 1,2-propylene carbonate to urea was 64.6% (the conversion of urea was 100%).

EXAMPLE 16

The procedure of Example 15 was followed except that 228.3 g (3.00 mole) of 1,2-propylene glycol was charged to the reactor. The reaction vessel was cooled after the reaction was stopped and 225.9 g of reaction solution was obtained. Gas-chromatography analysis showed that the amount of unreacted 1,2-propylene glycol was 156.2 g and the amount of produced 1,2-propylene carbonate was 92.9 g.

The conversion of 1,2-propylene glycol was 31.6% (theoretical conversion is 33.3%). The selectivity of 1,2-propylene carbonate to the 1,2-propylene glycol reacted was 96.0%. The selectivity of 1,2-propylene carbonate to urea was 91.0% (the conversion of urea was 100%).

EXAMPLE 17

The procedure of Example 15 was followed except that the reaction was carried out at 150° C. for 6 hours. The reactor was cooled after the reaction was stopped and 142.2 g of reaction solution was obtained. Gas-chromatography analysis showed that the amount of unreacted 1,2-propylene glycol was 40.6 g and the amount of produced 1,2-propylene carbonate was 92.9 g.

The conversion of 1,2-propylene glycol was 62.9% (theoretical conversion is 66.7%). The selectivity of 1,2-propylene carbonate to the 1,2-propylene glycol reacted was 96.7%. The selectively of 1,2-propylene carbonate to urea was 91.3% (the conversion of urea was 100%).

EXAMPLE 18

The procedure of Example 15 was followed except that 15 g of zinc oxide was charged into the reactor and the reaction was carried out at 160 ° C. The reaction vessel was cooled after the reaction was stopped and 154.9 g of reaction solution was obtained. Gas-chromatography analysis showed that the amount of unreacted 1,2-propylene glycol was 42.4 g and the amount of produced 1,2-propylene carbonate was 90.6 g.

The conversion of 1,2-propylene glycol was 62.7% (theoretical conversion is 66.7%). The selectivity of 1,2-propylene carbonate to the 1,2-propylene glycol reacted was 94.3%. The selectivity of 1,2-propylene carbonate to urea was 88.7% (the conversion of urea was 100%).

EXAMPLE 19

The procedure of Example 15 was followed except that 135.2 g (1.50 mole) of 1,2-butylene glycol was charged into the reactor. The reaction vessel was cooled after the reaction was stopped and 164.6 g of reaction solution was obtained. Gas-chromatography analysis showed that the amount of unreacted butylene glycol was 50.6 g and the amount of produced 1,2-butylene carbonate was 107.0 g.

The conversion of 1,2-butylene glycol was 62.5% (theoretical conversion is 66.7%). The selectivity of 1,2-butylene carbonate to the 1,2-butylene glycol reacted was 98.3%. The selectivity of 1,2-butylene carbonate to urea was 92.2% (the conversion of urea was 100%).

EXAMPLES 20–26

The procedure of Example 15 was followed except that different catalysts of zinc or magnesium were charged into the reactor. The catalyst used and the results obtained are shown in Table 2. The conversion of urea was 100% for each example of Table 2.

TABLE 2

| Example No. | Catalyst | Reacted solution | | | Glycol conversion | Carbonate selectivity | |
|---|---|---|---|---|---|---|---|
| | | Whole | Glycol | Carbonate | | to glycol | to urea |
| 20 | zinc powder | 145.1 g | 52.9 g | 74.5 g | 53.7% | 90.6% | 73.0% |
| 21 | zinc carbonate | 141.7 | 42.6 | 91.4 | 62.7 | 95.2 | 89.5 |
| 22 | zinc chloride | 141.1 | 43.2 | 89.6 | 62.2 | 94.1 | 87.8 |
| 23 | zinc acetate | 141.6 | 43.2 | 90.2 | 62.2 | 94.6 | 88.3 |
| 24 | zinc nitrate | 140.9 | 42.5 | 90.7 | 62.8 | 94.3 | 88.8 |
| 25 | magnesium oxide | 140.2 | 42.5 | 89.4 | 62.8 | 93.0 | 87.6 |
| 26 | magnesium acetate | 141.3 | 43.1 | 90.0 | 62.3 | 94.2 | 88.1 |

EXAMPLE 27

A 300-ml three-necked flask, equipped with a stirrer, reflux condenser and thermometer, was charged with 60.1 g (1.00 mole) of urea, 77.6 g (1.25 mole) of ethylene glycol and 3.0 g of lead dioxide. The reaction was carried out at 145° C. for 3 hours at a pressure of 100 mmHg with stirring and refluxing to remove the ammonia produced. After the completion of the reaction, 96.2 g of reacted solution was obtained by cooling the reaction solution. Gas-chromatography analysis showed that the amount of unreacted ethylene glycol was 17.3 g and the amount of produced ethylene carbonate was 76.6 g.

The conversion of ethylene glycol was 77.7% (theoretical conversion is 80.0%). The selectivity of ethylene carbonate to the ethylene glycol reacted was 89.6%. The selectivity of ethylene carbonate to urea was 87.0% (the conversion of urea was 100%).

EXAMPLE 28

The same reactor as in Example 27 was charged with 60.1 g (1.00 mole) of urea, 77.6 g (1.25 mole) of ethylene glycol and 3.0 g of calcium oxide. The reaction was carried out at 135° C. for 4 hours at a pressure of 80 mmHg with stirring and refluxing to remove the ammonia produced. After the completion of the reaction, 99.7 g of reacted solution was obtained by cooling the reaction solution. Gas-chromatography analysis showed that the amount of unreacted ethylene glycol was 21.6 g and the amount of produced ethylene carbonate was 70.6 g.

The conversion of ethylene glycol was 72.2% (theoretical conversion is 80.0%). The selectivity of ethylene carbonate to the ethylene glycol reacted was 88.9%. The selectivity of ethylene carbonate to urea was 80.2% (the conversion of urea was 100%).

EXAMPLE 29

A 500-ml three-necked flask, equipped with a stirrer, reflux condenser and thermometer, was charged with 60.1 g (1.00 mole) of urea, 186.2 g (3.00 mole) of ethylene glycol and 3.0 g of lead monoxide. The reaction was carried out at 145° C. for 4 hours at a pressure of 150 mmHg with stirring and refluxing to remove the ammonia produced. After the completion of the reaction, 210.5 g of reacted solution was obtained by cooling the reaction solution. Gas-chromatography analysis showed that the amount of unreacted ethylene glycol was 125.7 g and the amount of produced ethylene carbonate was 75.1 g.

The conversion of ethylene glycol was 32.5% (theoretical conversion is 33.3%). The selectivity of ethylene carbonate to the ethylene glycol reacted was 87.4%. The selectivity of ethylene carbonate to urea was 85.3% (the conversion of urea was 100%).

EXAMPLE 30

A 300-ml three-necked flask, equipped with a stirrer, reflux condenser and thermometer, was charged with 60.1 g (1.00 mole) of urea, 152.2 g (2.00 mole) of 1,2-propylene glycol and 1.5 g of lead dioxide. The reaction was carried out at 165° C. for 2 hours at a pressure of 320 mmHg with stirring and refluxing of the produced ammonia. After the reaction, 185.2 g of reacted solution was obtained by cooling the reactor. Gas-chromatography analysis showed that the amount of unreacted 1,2-propylene glycol was 77.2 g and the amount of produced 1,2-propylene carbonate was 95.9 g.

The conversion of 1,2-propylene glycol was 49.3% (theoretical conversion is 50.0%). The selectivity of 1,2-propylene carbonate to the 1,2-propylene glycol reacted was 95.2%. The selectivity of 1,2-propylene carbonate to urea was 93.9% (the conversion of urea was 100%).

EXAMPLE 31

The procedure of Example 30 was followed except that 1.5 g of calcium oxide was charged to the reactor. The reaction vessel was cooled after the reaction was stopped and 179.1 g of reaction solution was obtained. Gas-chromatography analysis showed that the amount of unreacted 1,2-propylene glycol was 76.9 g and the amount of produced 1,2-propylene carbonate was 97.4 g.

The conversion of 1,2-propylene glycol was 49.5% (theoretical conversion is 550.0%). The selectivity of 1,2-propylene carbonate to the 1,2-propylene glycol reacted was 96.4%. The selectivity of 1,2-propylene carbonate to urea was 95.4n (the conversion of urea was 100%).

EXAMPLES 32-36

The procedure of Example 30 was followed except that different catalysts of zinc or magnesium were charged into the reactor. The catalyst used and the results obtained are shown in Table 3. The conversion of urea was 100n for each example of Table 3.

TABLE 3

| Example No. | Catalyst | Reacted solution | | | Glycol conversion | Carbonate selectivity | |
|---|---|---|---|---|---|---|---|
| | | Whole | Glycol | Carbonate | | to glycol | to urea |
| 32 | lead tetra-acetate | 187.3 g | 77.5 g | 93.6 g | 49.1% | 93.4% | 91.7% |
| 33 | lead carbonate | 190.2 | 78.1 | 92.4 | 48.7 | 92.9 | 90.5 |
| 34 | lead di-ethoide | 189.3 | 77.6 | 93.9 | 49.0 | 93.9 | 92.0 |
| 36 | calcium chloride | 189.5 | 76.9 | 93.5 | 49.5 | 92.5 | 91.6 |

What I claim is:

1. A process for producing alkylene carbonates which comprises reacting urea and glycols described by the general formula RCH(OH) CH$_2$ OH; where R represents hydrogen or an alkyl group containing 1 to 4 carbons, using a catalyst containing at least one metal selected from zinc, magnesium, lead and calcium.

2. A process for producing alkylene carbonates which comprises reacting, at a temperature of 120°–240° C., urea and glycols described by the general formula RCH(OH) Ch$_2$OH; wherein R represents hydrogen or an alkyl group containing 1 to 4 carbons, at a pressure of 60–600 mm Hg absolute and in the presence of one or more catalysts selected from the group consisting of zinc, magnesium, lead and calcium.

3. A process according to claim 1 wherein the reaction is carried out by feeding reactants into the reaction mixture at a molar ratio of glycol to urea in the range of 1 to 5.

4. A process according to claim 1 wherein the glycol is ethylene glycol.

5. A process according to claim 1 wherein the reaction is carried out using a catalyst containing zinc and/or magnesium.

6. A process according to claim 1 wherein the reaction is carried out using a catalyst containing lead and/or calcium.

* * * * *